United States Patent
Wenderoth

(10) Patent No.: US 11,738,164 B2
(45) Date of Patent: Aug. 29, 2023

(54) PREFLUSHING UNIT FOR CARRYING OUT A PREFLUSHING OPERATION IN A BREATHING GAS CIRCUIT OF A CLOSED-CIRCUIT RESPIRATOR

(71) Applicant: Dräger Safety AG & Co. KGaA, Lübeck (DE)

(72) Inventor: Kurt Wenderoth, Ratzeburg (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 476 days.

(21) Appl. No.: 16/772,493

(22) PCT Filed: Nov. 19, 2018

(86) PCT No.: PCT/EP2018/081714
§ 371 (c)(1),
(2) Date: Jun. 12, 2020

(87) PCT Pub. No.: WO2019/115162
PCT Pub. Date: Jun. 20, 2019

(65) Prior Publication Data
US 2020/0398017 A1    Dec. 24, 2020

(30) Foreign Application Priority Data
Dec. 15, 2017 (DE) ..................... 10 2017 011 623.7

(51) Int. Cl.
*A61M 16/10* (2006.01)
*A61M 16/08* (2006.01)
(Continued)

(52) U.S. Cl.
CPC .... *A61M 16/1015* (2014.02); *A61M 16/0891* (2014.02); *A61M 16/201* (2014.02); *A62B 7/02* (2013.01); *A62B 9/02* (2013.01)

(58) Field of Classification Search
CPC .............. F16K 7/075; A61M 16/0891; A61M 16/1015; A61M 16/201; A61M 16/22; A62B 9/02; A62B 18/10
See application file for complete search history.

(56) References Cited

U.S. PATENT DOCUMENTS 2,247,363 A * 7/1941 Dunn ..................... F16K 15/14
137/247
2,617,414 A * 11/1952 Hollmann ................ A62B 9/02
128/205.12
(Continued)

FOREIGN PATENT DOCUMENTS

CN    202982970 U    6/2013
CN    204050578 U    12/2014
(Continued)

*Primary Examiner* — Kathryn E Ditmer
(74) *Attorney, Agent, or Firm* — McGlew and Tuttle, P.C.

(57) ABSTRACT

A preflushing unit (10) preflushes a breathing gas circuit (210) of a closed-circuit respirator (200). A basic body (20) has an inlet port (22), feeding breathing gas from a breathing gas supply (220), an outlet port (24) discharging breathing gas into the breathing circuit, and a flow section (32) fluid connecting a valve chamber (30). A valve body (40) with a sealing surface (42) is arranged in the valve chamber (30). An elastomer body (50) with a counter-sealing surface (52) in the valve chamber, fluid tight separates the flow section from a control section (34). The counter-sealing surface acts with a sealing force against the valve body for sealing the flow section. A control port (26) of the basic body provides a controlled feed of breathing gas from the breathing gas supply into the control section for pressure equalization between the flow section and the control section.

12 Claims, 3 Drawing Sheets

(51) Int. Cl.
*A61M 16/20* (2006.01)
*A62B 7/02* (2006.01)
*A62B 9/02* (2006.01)

(56) References Cited

U.S. PATENT DOCUMENTS

| | | | | |
|---|---|---|---|---|
| 2,622,620 | A | * 12/1952 | Annin | F16K 7/075 |
| | | | | 251/5 |
| 3,145,967 | A | * 8/1964 | Gardner | F16K 7/075 |
| | | | | 251/30.05 |
| 3,354,970 | A | * 11/1967 | Lummus | E21B 21/08 |
| | | | | 175/218 |
| 3,489,144 | A | * 1/1970 | Dibelius | A62B 7/10 |
| | | | | 128/205.12 |
| 3,502,099 | A | 3/1970 | Wilson | |
| 3,575,167 | A | * 4/1971 | Michielsen | A62B 7/10 |
| | | | | 55/482 |
| 3,624,801 | A | * 11/1971 | Gannon | F16K 7/075 |
| | | | | 251/5 |
| 3,952,773 | A | * 4/1976 | Hahn | A62B 9/027 |
| | | | | 137/895 |
| 4,023,772 | A | * 5/1977 | Ratelband | F16K 7/075 |
| | | | | 251/5 |
| 4,796,804 | A | * 1/1989 | Weiss | B05B 1/3006 |
| | | | | 239/203 |
| 5,050,593 | A | * 9/1991 | Poon | A61M 16/0858 |
| | | | | 128/205.24 |
| 5,090,660 | A | * 2/1992 | Ratelband | F16K 7/075 |
| | | | | 251/61.1 |
| 5,857,661 | A | * 1/1999 | Amada | F16K 7/075 |
| | | | | 137/467.5 |
| 6,053,191 | A | * 4/2000 | Hussey | F16K 7/075 |
| | | | | 175/218 |
| 7,703,477 | B2 | 4/2010 | Cook et al. | |
| 2006/0163506 | A1 | * 7/2006 | Cook | G05D 7/012 |
| | | | | 251/5 |
| 2011/0048423 | A1 | * 3/2011 | Leffel | F16K 3/26 |
| | | | | 128/205.24 |

FOREIGN PATENT DOCUMENTS

| | | |
|---|---|---|
| DE | 859994 C | 12/1952 |
| DE | 8599940 C | 12/1952 |
| DE | 889115 C | 9/1953 |
| DE | 919629 C | 10/1954 |
| DE | 919630 C | 10/1954 |
| DE | 969287 C | 5/1958 |
| DE | 1157927 B | 11/1963 |
| DE | 2404062 B2 | 9/1977 |
| FR | 1416992 A | 11/1965 |
| GB | 1286840 A | 11/1972 |
| GB | 2525973 A * 11/2015 | ............... A62B 7/02 |

\* cited by examiner

PREFLUSHING UNIT FOR CARRYING OUT A PREFLUSHING OPERATION IN A BREATHING GAS CIRCUIT OF A CLOSED-CIRCUIT RESPIRATOR

CROSS REFERENCE TO RELATED APPLICATIONS

This application is a United States National Phase Application of International Application PCT/EP2018/081714, filed Nov. 19, 2018, and claims the benefit of priority under 35 U.S.C. § 119 of German Application 10 2017 011 623.7, filed Dec. 15, 2017, the entire contents of which are incorporated herein by reference.

TECHNICAL FIELD

The present invention pertains to a preflushing unit for carrying out a preflushing operation in case of a breathing gas circuit of a closed-circuit respirator, to a gas-carrying device for a closed-circuit respirator as well as to a process for a preflushing operation in case of such a gas-carrying device.

TECHNICAL BACKGROUND

It is known that closed-circuit respirators are used to protect users of these devices from breathing in toxic gases in harsh environments. In order to be able to guarantee the user an as long as possible duration of use, these closed-circuit respirators are provided with a breathing gas circuit which feeds incoming air to the mouth of the user and leads away exhaust air as exhaled air from the mouth of the user. In order to achieve the long duration of use, respirator components that are used to purify the exhaust air from the mouth of the user, on the one hand, and can guarantee the adding of oxygen or normal air to the purified breathing air, on the other hand, are provided within the closed-circuit respirator. It is thus ensured that the reduction correlates with a filling up with oxygen due to the removal of $CO_2$ in the purification process and a long duration of use thus becomes possible for the closed-circuit operation of the closed-circuit respirator.

A drawback of the prior-art solutions is that a relatively great effort has to be made in order to keep the breathing gas circuit free from undesired gas residues at the beginning of use using such a closed-circuit respirator. This refers especially to an increased nitrogen content and/or an increased $CO_2$ content in the breathing gas circuit. In order to avoid the first breaths from now taking place with an unwanted gas mixture in the breathing gas circuit, it is mandatorily stipulated depending on the particular country of use that a so-called preflushing operation with breathing gas has to be carried out. The breathing gas flowing through will displace residual gas remaining during this preflushing operation with undesired gas mixtures from the breathing gas circuit, and a defined gas composition in the breathing gas circuit will thus be able to be available at the end of the preflushing operation for the user at the beginning of the use. Complicated mechanical solutions with spring systems, but also electrical or electronic preflushing devices, which have a correspondingly complicated, expensive and large-volume configuration, have been known up to now in order to guarantee this.

SUMMARY

An object of the present invention is to eliminate the above-described drawbacks at least partially. In particular, the object of the present invention is to be able to provide an as automated as possible preflushing for the breathing gas circuit in case of a closed-circuit respirator in a cost-effective and simple manner.

The above object is accomplished by a preflushing unit, a gas-carrying device, as well as a process according to the invention. Features and details that are described in connection with the preflushing unit according to the present invention are here obviously also valid in connection with the gas-carrying device according to the present invention as well as in connection with the process according to the present invention and vice versa, so that reference is made or may always be made mutually to the individual aspects of the present invention with regard to the disclosure.

A preflushing unit is used for carrying out a preflushing operation in case of a breathing gas circuit of a closed-circuit respirator according to the present invention. For this purpose, the preflushing unit has a basic body with an inlet port for the feed of breathing gas from a breathing gas supply. In addition, an outlet port for the discharge of breathing gas into the breathing gas circuit is provided at the basic body. The inlet port and the outlet port are in fluid-communicating connection with one another via a flow section of a valve chamber in the basic body. In addition, a valve body with a sealing surface is arranged in this valve chamber. Further, an elastomer body with a counter-sealing surface, which separates the flow section in a fluid-tight manner from a control section and consists of an elastic material, is arranged in the valve chamber. Due to the selection of an elastic material, the elastomer body can act on the counter-sealing surface with a sealing force against the sealing surface of the valve body to seal the flow section. Further, a control port is provided at the basic body for the controlled feed of breathing gas from the breathing gas supply into the control section to be able to guarantee a pressure equalization between the flow section and the control section.

Regardless of any mechanical and/or electrical or electronic solutions, the above explanation of the preflushing unit now makes it possible to be able to provide a pneumatic control, and especially a pneumatic regulation or pneumatic control. The course of the preflushing with a preflushing unit according to the present invention will be explained in detail below in order to be able to explain the relatively complicated operations in more detail.

At the beginning of the use of a closed-circuit respirator, a corresponding breathing gas supply must be provided. Such a breathing gas supply is usually arranged within a pressurized cylinder and has oxygen as breathing gas with a high overpressure of, for example, about 200 bar. The preflushing operation must be carried out to be able to now displace undesired gas mixtures in a breathing gas circuit within the closed-circuit respirator. For this purpose, the breathing gas supply is connected to the breathing gas circuit and can in this way propagate its pressure into the preflushing unit. The breathing gas and hence also the pressure reach the basic body of the preflushing unit via the inlet port, especially via a pressure reducer arranged upstream. The medium pressure present at this time or at this location leads to the elastomer body being moved outwards into the control section based on the medium pressure of the breathing gas against the elastic prestressing force of the elastomer body and thus the counter-sealing surface of the elastomer body is removed from the sealing surface of the valve body. The sealing, which was previously formed between the counter-sealing surface of the valve body and of the elastomer body and the sealing surface of the valve body, is cancelled out in this manner due to the application of the medium pressure via the inlet port, so that now the breathing gas can flow through the valve chamber and thus through the flow section to the outlet port due to the increased medium pressure. As this will be explained later with reference to a gas-carrying device according to the present invention, the outlet port is now in connection with a breathing gas circuit, so that at this time now the breathing gas can enter the breathing gas circuit via the preflushing unit and through the open flow section via the outlet port and displace undesired gas mixtures there.

The above-described beginning of the preflushing shows how this breathing gas, due to its entry, propagates into the breathing gas circuit and displaces undesired gas mixtures there. The second core idea of a preflushing unit according to the present invention is now used for an as automated as possible ending of this preflushing operation in order to ensure that an unnecessarily large quantity of breathing gas is not used or wasted for the preflushing operation. The basic body is equipped with a control port for this purpose. The control port is likewise supplied with breathing gas from the breathing gas supply, but is provided with a lower rate of pressure rise. This may be provided, on the one hand, by a defined smaller passage opening in the control port, by correspondingly longer or smaller feed lines to the control port or else also by the dispensing unit in such a control port, which dispensing unit will be explained in more detail later. While the medium pressure now continues more rapidly via the inlet port into the valve chamber and there into the flow section, a propagation of the same medium pressure into the control port and thus into the control section of the valve chamber will take place in a markedly slower manner. Consequently, the elastomer body will thus bulge outwards at the beginning of the preflushing operation, so that the control section is made smaller and the flow section is made larger in order to open the desired fluid-communicating connection to the outlet port. Over the course of the preflushing operation, the breathing gas now also enters the control section of the valve chamber more and more via the control port. A pressure equalization between the internal pressure in the control section and the internal pressure in the flow section will result over time. As soon as the pressure, which is identical in both positions since the breathing gas is in connection with the medium pressure port of the breathing gas supply, is equalized, the elastomer body will be moved back into its starting position. In this starting position, the control section of the valve chamber is made larger again and correspondingly the flow section is made smaller by the same amount. Due to the pressure equalization, the only force that still acts on the elastomer body is now the elastic restoring force of the elastic material, so that now the counter-sealing surface is again pressed against the sealing surface of the valve body and the flow section is sealed in this manner. This time defines the end of the preflushing operation, since the fluid-communicating connection to the outlet port of the basic body has now been interrupted by this sealing operation, so that a further outflow of breathing gas through the preflushing unit is now prevented.

As is apparent from the above procedures, dispensing with any electronic or electrical control and also dispensing with mechanical prestressing units such as springs or similar valves, a pneumatic and automated control or regulation in the form of the control of the preflushing operation can be carried out. Geometrically and structurally, due to the flow rates or the corresponding volume flows at the control port and at the inlet port or at the outlet port, it is possible to predict and to set in a defined manner how large the quantity of breathing gas shall be for the preflushing operation or for how long this preflushing operation will be carried out.

A simple, cost-effective and small preflushing unit can thus be provided on the basis of the hitherto known highly complicated solutions. In particular, the automation due to the pneumatic control can be achieved in a simple and cost-effective manner as well as with high operating reliability due to the reduced complexity.

It may be advantageous when in case of a preflushing unit according to the present invention, the inlet port and the outlet port have an identical or essentially identical flow cross section. This refers especially also to the flow cross section within the flow section, preferably in its fully open position at the beginning of the preflushing operation. Undesired flow resistances can be avoided due to the constancy of a flow cross section over the course through the flow section of the basic body, so that in particular the time for the preflushing operation and the preflushing quantity of breathing gas can be predicted in a defined manner in a more defined and more predictable manner. A fast and above all reliable as well as predefined preflushing can be effectively achieved in this manner.

Another advantage can be achieved when the elastomer body in a preflushing unit according to the present invention has a rotationally symmetrical counter-sealing surface, especially a rotationally symmetrical configuration. A rotationally symmetrical configuration of the elastomer body makes possible an especially simple and cost-effective manufacture. In addition, the pressure distribution about a rotationally symmetrical elastomer body is especially uniform, so that a corresponding sealing functionality can be provided in a simpler, more cost-effective manner and especially with high reliability. The rotationally symmetrical configuration also preferably leads to the counter-sealing surface being fully in contact with the corresponding sealing surface of the valve body.

Another advantage can be achieved when the valve body in case of a preflushing unit according to the present invention has a rotationally symmetrical sealing surface, especially an at least partially rotationally symmetrical configuration. The present embodiment is especially combined with the preflushing unit according to the above paragraph. The valve body can also be manufactured here in an especially simple and cost-effective manner. The flow geometry as well as the pressure distribution are also configured especially advantageously in case of the rotationally symmetrical configuration of the sealing surface. Not least, the full contact of the counter-sealing surface in a rotationally symmetrical manner with the corresponding sealing surface of the valve body is again advantageous here.

Another advantage may be when the valve body is arranged, especially as a valve cone, centrally or essentially centrally in the flow section in a preflushing unit according to the present invention. The central arrangement thus makes possible a full flowthrough, wherein the valve body is preferably formed along the flow axis within the flow section. Improved extensive flow around may also lead here to a lower flow resistance, so that the predefined selection of the preflushing operation can be carried out with higher reliability. Due to the symmetrical and extensive flow around, undesired flow turbulences are avoided or reduced to a minimum.

Another advantage can be achieved when the sealing surface in case of a preflushing unit according to the present invention is arranged at a widening sealing section of the valve body. This means that the valve body preferably runs closer together in a cone-shaped manner before the sealing section and/or after the sealing section. The space within the flow section is thus widened, so that the already explained improved flow conditions with preferably constant free flow cross sections can especially be achieved in case of an open flow section.

Another advantage may be when in case of a preflushing unit according to the present invention the basic body has an auxiliary port in fluid-communicating connection with the control section for a fluid-communicating connection to an auxiliary control volume. Due to its size, the control section, on the one hand, and the control port due to the feed rate and thus the rate of propagation of the medium pressure of the breathing gas, on the other hand, will precisely define when the end of the preflushing operation is reached due to the end of the pressure equalization. If an extension of this preflushing operation is desired, then an additional auxiliary control volume may now be provided via an auxiliary port according to this embodiment, so that extension up to the end of the pressure equalization is achieved in case of constant rate of propagation of the medium pressure through the control port, since a greater volume, i.e., also the auxiliary control volume can or must now be filled with the corresponding medium pressure in case of a constant flow rate. Since different auxiliary control volumes can now be used via the auxiliary port, a simple, flexible and especially cost-effective adaptation to different standard requirements in different countries is possible due to the selection of auxiliary control volumes of different sizes.

It is also advantageous when in a preflushing unit according to the present invention, a dispensing unit is arranged, especially as a separate component, in the control port with a dispensing opening for the passage of breathing gas from the breathing gas supply into the control section. Such a dispensing unit is especially configured as a separate component and can thus be produced in a simple and cost-effective manner with narrow tolerance ranges. The dispensing opening may in this case be specific to the particular dispensing unit, so that different dispensing units with dispensing openings of correspondingly different sizes for different preflushing requirements can be provided for different standard requirements. Using the dispensing unit with a dispensing opening makes it possible to reduce the tolerance accuracy for the manufacture of the basic body and to be able to use a cost-effective and simple manufacturing process here.

It may also be advantageous when fastening devices are arranged in a preflushing unit according to the present invention at the inlet port, at the outlet port and/or at the control port for a fluid-tight fastening of breathing gas tubes. These are especially standardized fastening devices, which may have, for example, plug-type and/or clamping connections. The fastening devices are preferably provided at all ports of the basic body.

A gas-carrying device for a closed-circuit respirator, having a mounting port for a breathing gas supply, is also a subject of the present invention. Further, a refill port is provided in the breathing gas circuit of the closed-circuit respirator. The mounting port is connected to the inlet port in a fluid-communicating manner via a preflushing outlet and to the control port of a preflushing unit via a control outlet. Further, the outlet port of the preflushing unit is connected to the refill port in a fluid-communicating manner. The connection to the refill port is in this case preferably provided by bypassing a corresponding refill valve assembly, so that the desired preflushing function can be guaranteed by means of such a refill valve especially independently of a continuous refilling or a need-based refilling. By using a preflushing unit according to the present invention, a gas-carrying device according to the present invention now offers the same advantages as they were explained in detail with reference to a preflushing unit according to the present invention.

A gas-carrying device according to the present invention can be perfected in that the mounting port has a pressure reducer for reduction of the high pressure to a medium pressure in the breathing gas supply. A high pressure of about 200 bar is usually present within the breathing gas supply. Due to the use of a pressure reducer, this high pressure can be reduced to a medium pressure to be able to guarantee the desired preflushing function in case of a simple and cost-effective configuration of the individual components under the requirements of such a medium pressure atmosphere.

Another subject of the present invention is a process for a preflushing operation in a gas-carrying device according to the present invention, having the following steps:

Connection of the breathing gas supply to the mounting port, outflow of breathing gas via the preflushing outlet through the inlet port of the preflushing unit, through the flow section into the breathing gas circuit via the outlet port, and inflow of breathing gas via the control outlet and via the control port of the preflushing unit into the control section until pressure equalization is obtained with the flow section.

Due to the use of a gas-carrying device according to the present invention, the process according to the present invention offers the same advantages as they were explained in detail with reference to the gas-carrying device according to the present invention or with reference to the preflushing unit according to the present invention. The two steps of outflow as well as inflow here preferably run parallel in time until they have reached a pneumatic endpoint, namely the pressure equalization between the flow section and the control section.

Further advantages, features and details of the present invention appear from the following description, in which exemplary embodiments of the present invention are described in detail with reference of the drawings. In this case, the features mentioned in the claims and in the specification can each be essential to the present invention individually for themselves or in any combination.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
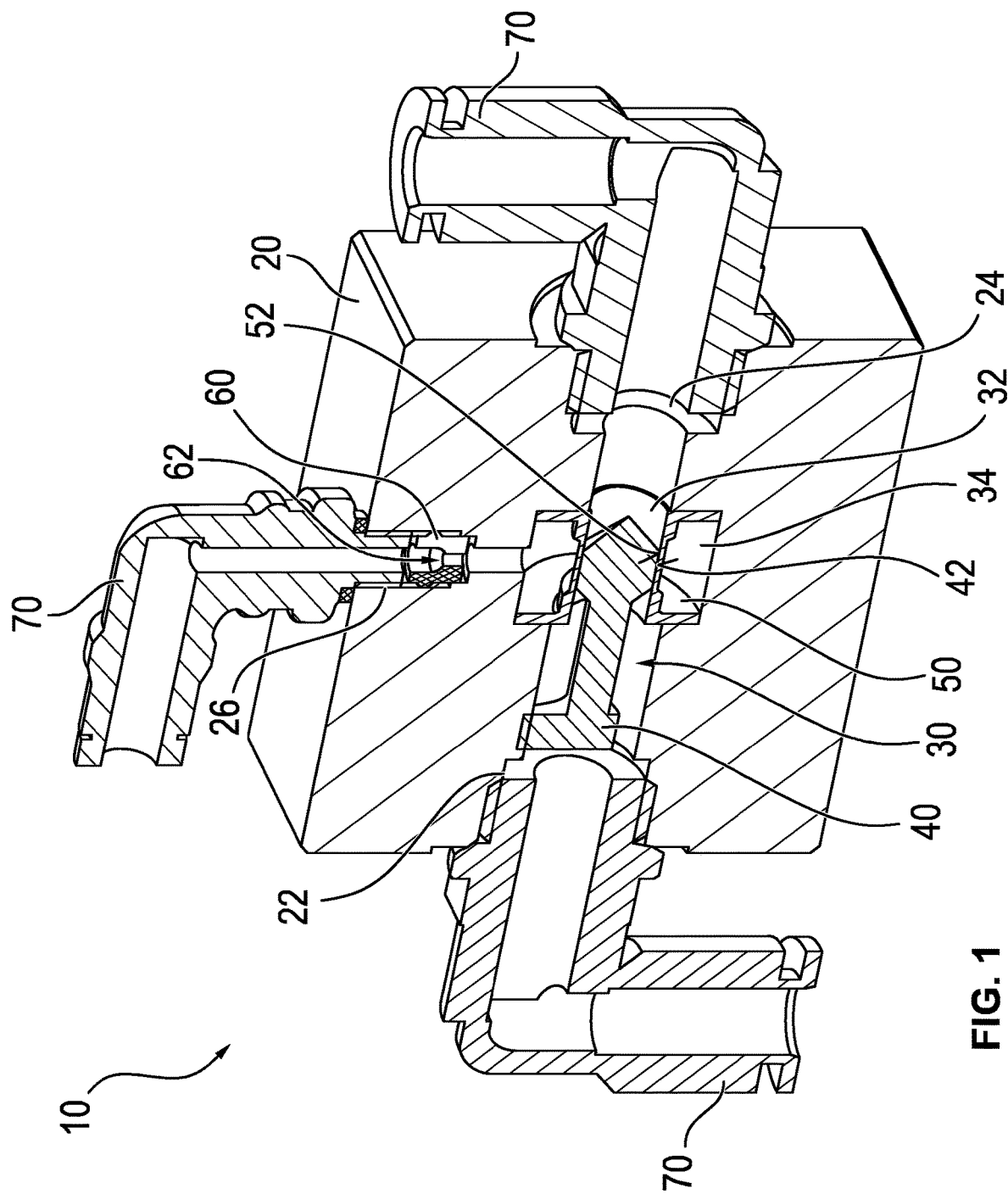
FIG. 1 is a schematic perspective cross sectional view showing a first embodiment of a preflushing unit according to the present invention.
Figure 2:
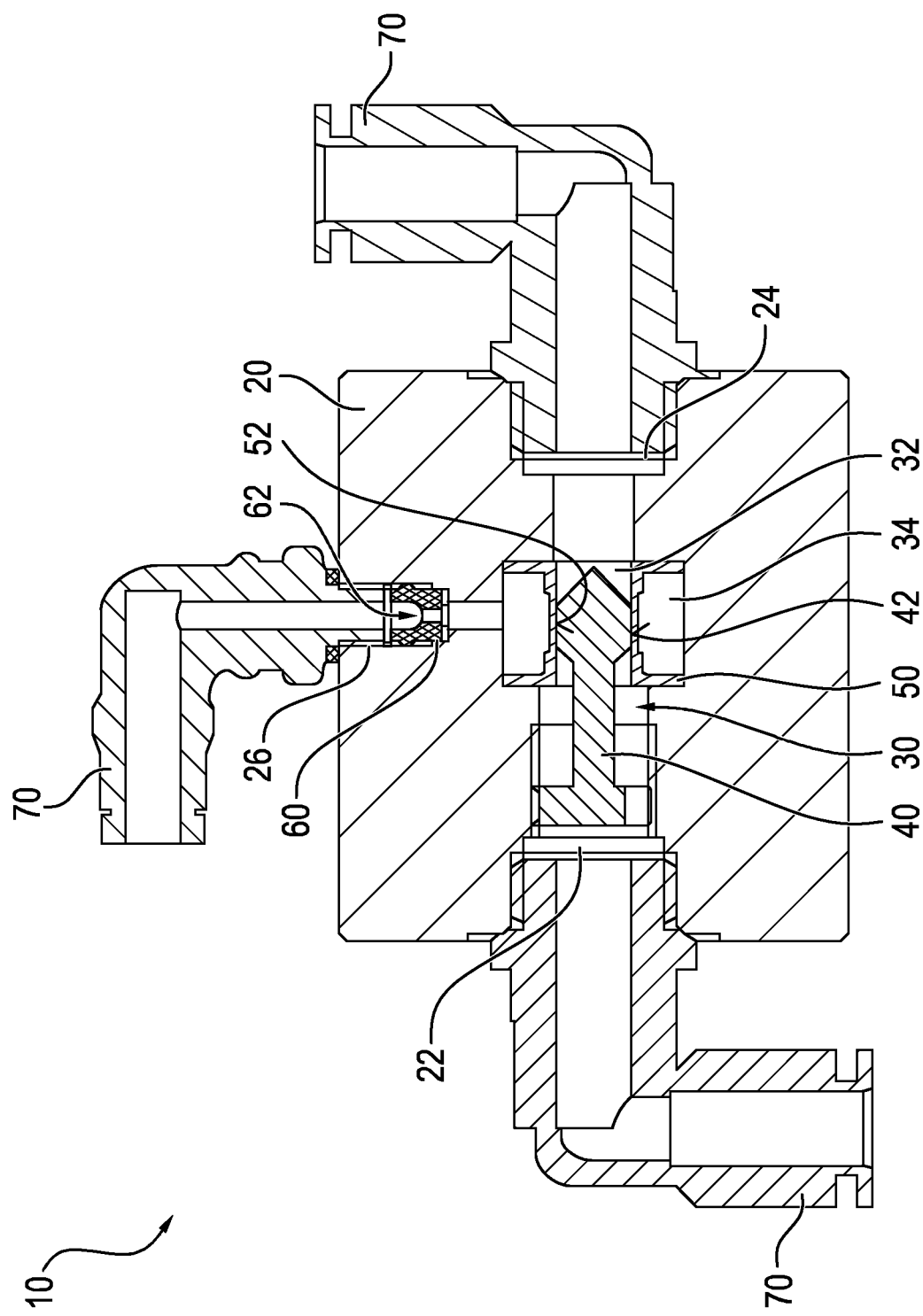
FIG. 2 is a schematic cross sectional view of the embodiment from FIG. 1.

Referring to the drawings, FIGS. 1 and 2 schematically show how a preflushing unit 10 can be configured. Based on these two views, it is again briefly explained how the preflushing operation takes place. As soon as the pressure, which is reduced, for example, to a medium pressure via a pressure reducer for the breathing gas, is applied, the breathing gas can flow into the inlet port 22 in the basic body 20 via the fastening device 70. As soon as this medium pressure and thus the breathing gas have reached the valve chamber 30, the elastic prestressing force of the elastomer body 50 is cancelled out due to the high internal pressure, so that the counter-sealing surface 52 is removed from the sealing surface 42 of the valve body and the flow section 32 is released. The breathing gas thus propagates further and flows further into the breathing gas circuit 210 via the outlet port 24 and the corresponding fastening device 70, as it is shown, for example, in FIG. 3.

The breathing gas and thus also the medium pressure are simultaneously in contact with the control port 26 of the basic body 20 also via the fastening device 70. As a result, a flow of the breathing gas will now flow into the control section 34 through the dispensing unit 60 and through a central and small dispensing opening 62 there. As soon as the medium pressure now continues to further propagate into the control section 34 and the corresponding internal pressure there rises, the elastomer body 50 is moved back into its position, as it is shown in FIG. 1. As soon as a pressure equalization has taken place between the control section 34 and the flow section 32, the elastomer body 50 again assumes the sealing position, as it is shown in FIGS. 1 and 2. As soon as this sealing has ended, the flow passage through the valve chamber 30 and there through the flow section 32 is blocked again, so that the preflushing operation is recognized as ended.

Figure 3:
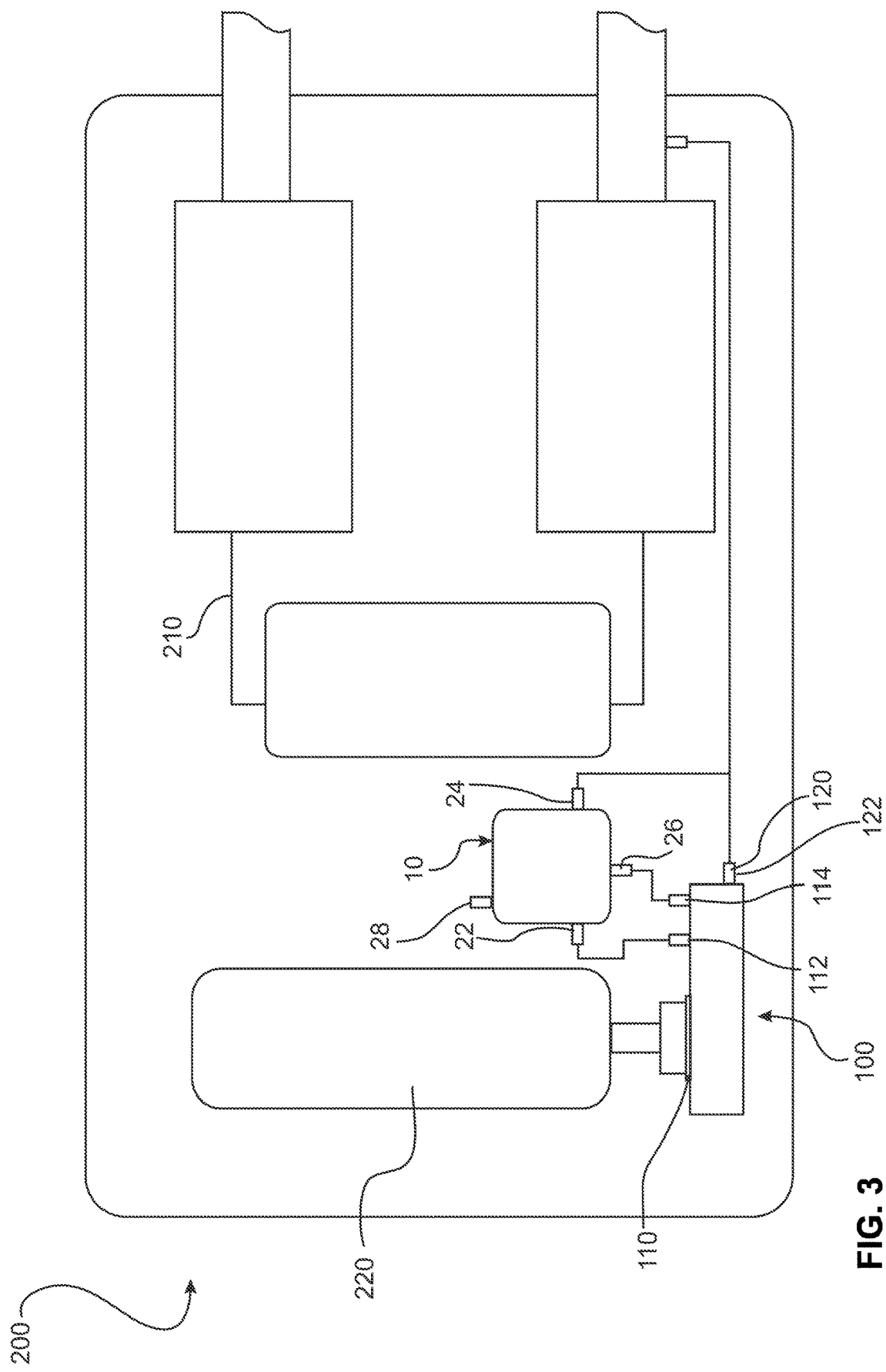
FIG. 3 is a schematic view of an embodiment of a gas-carrying device according to the present invention.

FIG. 3 schematically shows how such a preflushing unit 10 can be integrated into a closed-circuit respirator 200. A gas-carrying device 100, which can be connected to a high-pressure component in the form of a breathing gas supply 220 by means of a mounting port 110, is provided here. Between them, a pressure reducer is preferably connected. The lowered pressure of the breathing gas can now propagate into the breathing gas circuit 210 in the regular state via the refill port 120, for example, in a need-based control via a refill valve 122. The preflushing unit 10 is now intended, for example, in the embodiment of FIGS. 1 and 2 to be able to predefine the desired preflushing function at the beginning Starting from the mounting port 110, the breathing gas may now be applied to the inlet port 22 of the preflushing unit 10 via the preflushing outlet 112. The breathing gas and thus the medium pressure are also applied parallel in time and simultaneously to the control port 26 via the control outlet 114 of the gas-carrying device 100. The functionality within the preflushing unit 10 is in this case identical to the preflushing unit 10 described with reference to FIGS. 1 and 2.

Another advantage may be when in case of a preflushing unit 10 according to the present invention, the basic body 20 has an auxiliary port 28 in fluid-communicating connection with the control section 34 for a fluid-communicating connection to an auxiliary control volume. Due to its size, the control section 34, on the one hand, and the control port 26, due to the feed rate and thus the rate of propagation of the medium pressure of the breathing gas, on the other hand, will precisely define when the end of the preflushing operation is reached due to the end of the pressure equalization. If an extension of this preflushing operation is desired, then an additional auxiliary control volume may now be provided via the auxiliary port 28 according to this embodiment, so that extension up to the end of the pressure equalization is achieved in case of constant rate of propagation of the medium pressure through the control port 26, since a greater volume, i.e., also the auxiliary control volume can or must now be filled with the corresponding medium pressure in case of a constant flow rate. Since different auxiliary control volumes can now be used via the auxiliary port 28, a simple, flexible and especially cost-effective adaptation to different standard requirements in different countries is possible due to the selection of auxiliary control volumes of different sizes.

The above explanation of the embodiments describes the present invention exclusively within the scope of examples. Individual features of the embodiments, if they are technically meaningful, may, of course, be freely combined with one another, without going beyond the scope of the present invention.

While specific embodiments of the invention have been shown and described in detail to illustrate the application of the principles of the invention, it will be understood that the invention may be embodied otherwise without departing from such principles.

The invention claimed is:

1. A preflushing unit for carrying out a preflushing operation in a breathing gas circuit of a closed-circuit respirator, the preflushing unit comprising:
    a body with an inlet port for a feed of breathing gas from a breathing gas supply and with an outlet port for a discharge of breathing gas into the breathing gas circuit, wherein the inlet port and the outlet port are fluid connected to a valve chamber in the body via a flow section;
    a valve body with a sealing surface arranged in the valve chamber; and
    an elastomer body with a counter-sealing surface in the valve chamber, wherein the counter-sealing surface further fluid tight separates the flow section from a control section and is formed of an elastic material, wherein the counter-sealing surface is configured to act with a sealing force against the sealing surface of the valve body for closing a fluid pathway that extends between the inlet port and the outlet port via the flow section, wherein the body further has a control port for a controlled feed of breathing gas from the breathing gas supply into the control section at a lower rate of pressure rise than from the breathing gas supply into the flow section via the inlet port for pressure equalization between the flow section valve chamber and the control section;
    a gas carrying device having a mounting port configured to receive the breathing gas from the breathing gas supply, a preflushing outlet configured to transfer the breathing gas from the mounting port to the inlet port of the body, a refill port configured to transfer the breathing gas from the mounting port to the breathing gas circuit of the closed-circuit respirator, and a control outlet configured to transfer breathing gas from the mounting port to the control port of the body, the outlet port of the body being in fluid connection with the refill port.

2. The preflushing unit in accordance with claim 1, wherein the inlet port and the outlet port have an identical or essentially identical flow cross section.

3. The preflushing unit in accordance with claim 1, wherein the elastomer body has a rotationally symmetrical counter-sealing surface configuration.

4. The preflushing unit in accordance with claim 1, wherein the valve body has a rotationally symmetrical sealing surface configuration.

5. The preflushing unit in accordance with claim 1, wherein the valve body is arranged centrally or essentially centrally in the flow section.

6. The preflushing unit in accordance with claim 1, wherein the sealing surface is arranged at a widening sealing section of the valve body.

7. The preflushing unit in accordance with claim 1, wherein the body has an auxiliary port in fluid-communicating connection with the control section for a fluid-communicating connection to an auxiliary control volume.

8. The preflushing unit in accordance with claim 1, further comprising a dispensing unit arranged in the control port with a dispensing opening for passage of breathing gas from the breathing gas supply into the control section, the dispensing unit being a separate component, the body being configured to accept different dispensing units with dispensing openings of correspondingly different sizes.

9. The preflushing unit in accordance with claim 1, further comprising fastening devices arranged at the inlet port, at the outlet port and/or at the control port for a fluid-tight fastening of breathing gas tubes.

10. A closed-circuit respirator comprising:
a breathing gas circuit;
a preflushing unit comprising:
  a body with an inlet port for a feed of breathing gas from a breathing gas supply and with an outlet port for a discharge of breathing gas into the breathing gas circuit, wherein the inlet port and the outlet port are fluid connected to a valve chamber in the body via a flow section;
  a valve body with a sealing surface arranged in the valve chamber; and
  an elastomer body with a counter-sealing surface in the valve chamber, wherein the counter-sealing surface further fluid tight separates the flow section from a control section and is formed of an elastic material, wherein the counter-sealing surface is configured to act with a sealing force against the sealing surface of the valve body for closing the a fluid pathway that extends between the inlet port and the outlet port via the flow section, wherein the body further has a control port for a controlled feed of breathing gas from the breathing gas supply into the control section for pressure equalization between the flow section and the control section;
a gas-carrying device comprising a mounting port for the breathing gas supply, a refill port configured to discharge breathing gas into the breathing gas circuit, wherein the mounting port is fluid connected to the inlet port via a preflushing outlet and to the control port of the preflushing unit via a control outlet, the outlet port of the preflushing unit being further fluid connected to the refill port.

11. The closed-circuit respirator in accordance with claim 10, wherein the mounting port has a pressure reducer for the reduction of the high pressure in the breathing gas supply to a medium pressure.

12. A process for a preflushing operation in a closed-circuit respirator using a gas-carrying device and a preflushing unit,
the gas-carrying device comprising:
  a mounting port for a breathing gas supply, a refill port configured to discharge breathing gas into a breathing gas circuit of the closed-circuit respirator, wherein the mounting port is fluid connected to an inlet port of the preflushing unit via a preflushing outlet and to a control port of the preflushing unit via a control outlet, an outlet port of the preflushing unit being further fluid connected to the refill port,
the preflushing unit comprising:
  a body with the inlet port for a feed of breathing gas from the breathing gas supply and with the outlet port for a discharge of breathing gas into the breathing gas circuit, wherein the inlet port and the outlet port are fluid connected to a valve chamber in the body via a flow section; a valve body with a sealing surface arranged in the valve chamber; and an elastomer body with a counter-sealing surface in the valve chamber, wherein the counter-sealing surface further fluid tight separates the flow section from a control section and is formed of an elastic material, wherein the counter-sealing surface is configured to act with a sealing force against the sealing surface of the valve body for closing the a fluid pathway that extends between the inlet port and the outlet port via the flow section, wherein the body further has the control port for a controlled feed of breathing gas from the breathing gas supply into the control section for pressure equalization between the flow section and the control section,
the process comprising the steps of:
connecting the breathing gas supply to the mounting port;
providing an outflow of breathing gas via the preflushing outlet through the inlet port of the preflushing unit, through the flow section into the breathing gas circuit via the outlet port; and
providing an inflow of breathing gas via the control outlet and via the control port of the preflushing unit into the control section until pressure equalization is obtained with the flow section.

* * * * *